US00PP14656P29

(12) United States Plant Patent
Trees

(10) Patent No.: US PP14,656 P2
(45) Date of Patent: Mar. 30, 2004

(54) ANGELONIA PLANT NAMED 'BALANGDEPI'

(50) Latin Name: *Angelonia augustifolia*
Varietal Denomination: Balangdepi

(75) Inventor: Scott C. Trees, Shell Beach, CA (US)

(73) Assignee: Ball Horticultural Co., West Chicago, IL (US)

( * ) Notice: Subject to any disclaimer, the term of this patent is extended or adjusted under 35 U.S.C. 154(b) by 0 days.

(21) Appl. No.: 10/359,752

(22) Filed: Feb. 6, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Angelonia plant named 'Balangdepi', characterized by its upright and outwardly spreading plant habit; freely basal branching growth habit; and violet-colored flowers.

2 Drawing Sheets

Botanical classification/cultivar denomination: *Angelonia augustifolia* cultivar Balangdepi.

BACKGROUND OF THE INVENTION

The present Invention relates to a new and distinct cultivar of Angelonia plant, botanically known as *Angelonia hybrida*, and hereinafter referred to by the name 'Balangdepi'.

The new Angelonia is a product of a planned breeding program conducted by the Inventor in Arroyo Grande, Calif. The objective of the breeding program is to develop new vigorous Angelonia cultivars that have a freely basal branching growth habit and numerous flowers with attractive coloration.

The new Angelonia originated from a cross-pollination made by the Inventor in 2000 of a proprietary *Angelonia hybrida* selection identified as code number BFP-273, not patented, as the female, or seed parent, with an unnamed selection of *Angelonia integerimma*, not patented, as the male, or pollen parent. The cultivar Balangdepi was discovered and selected by the Inventor as a flowering plant within the progeny of the stated cross-pollination in a controlled environment in Arroyo Grande, Calif.

Asexual reproduction of the new cultivar by cuttings taken in Arroyo Grande, Calif. since June, 2000, has shown that the unique features of this new Angelonia are stable and reproduced true to type in successive generations.

SUMMARY OF THE INVENTION

The following traits have been repeatedly observed and are determined to be the unique characteristics of 'Balangdepi'. These characteristics in combination distinguish 'Balangdepi' as a new and distinct Angelonia cultivar:

1. Upright, outwardly spreading plant habit.
2. Freely basal branching growth habit.
3. Violet-colored flowers.

Compared to plants of the female parent selection, plants of the new Angelonia are more compact. Compared to plants of the male parent selection, plants of the new Angelonia are shorter and have a more freely basal branching habit.

Plants of the new Angelonia can be compared to plants of the cultivar Balangdeum, disclosed in U.S. Plant Pat. No. 12,040. In side-by-side comparisons conducted in West Chicago, Ill. plants of the new Angelonia differed from plants of the cultivar Balangdeum in the following characteristics:

1. Plants of the new Angelonia were more vigorous and larger than plants of the cultivar Balangdeum.
2. Plants of the new Angelonia had a more freely basal branching growth habit than plants of the cultivar Balangdeum.
3. Plants of the new Angelonia were more densely foliated than plants of the cultivar Balangdeum.
4. Plants of the new Angelonia had longer leaves than plants of the cultivar Balangdeum.
5. Plants of the new Angelonia were more freely flowering than plants of the cultivar Balangdeum.

BRIEF DESCRIPTION OF THE PHOTOGRAPHS

The accompanying colored photographs illustrate the overall appearance of the new Angelonia, showing the colors as true as it is reasonably possible to obtain in colored reproductions of this type. Colors in the photographs differ from the color values cited in the detailed botanical description which accurately describe the colors of the new Angelonia.

The photograph on the first sheet comprises a side perspective view of a flowering plant of 'Balangdepi' grown in a container.

The photograph on the second sheet comprises a close-up view of a typical flowering raceme of 'Balangdepi'.

DETAILED BOTANICAL DESCRIPTION

The cultivar Balangdepi has not been observed under all possible environmental conditions. The phenotype may vary somewhat with variations in environment such as temperature and light intensity without, however, any variance in genotype.

The aforementioned photographs and following observations and measurements describe plants grown in West Chicago, Ill. under commercial practice in a polycarbonate-covered greenhouse with day temperatures ranging from 24 to 29° C., night temperatures ranging from 17 to 21° C. and light levels ranging from 6,000 to 10,000 footcandles. Rooted young plants were planted in 10-cm containers and had been growing for about 14 weeks when the photographs and the description were taken.

In the following description, color references are made to The Royal Horticultural Society Colour Chart, 2001 Edition, except where general terms of ordinary dictionary significance are used.

Botanical classification: *Angelonia hybrida* cultivar Balangdepi.

Parentage:

*Female parent.*—Proprietary *Angelonia hybrida* selection identified as code number BFP-273, not patented.

*Male parent.*—Unnamed selection of *Angelonia integerimma* selection identified as code number BFP-272, not patented.

Propagation:

*Type.*—Cuttings.

*Time to initiate roots.*—About 7 days at 18° C.

*Time to produce a rooted cutting.*—About 21 days at 18° C.

*Root description.*—Fibrous; whitish in color.

Plant description:

*General appearance.*—Upright and outwardly spreading plant habit; vigorous. Freely basal branching growth habit, about six flowering stems develop per plant.

*Plant height.*—About 47.7 cm.

*Plant diameter or spread.*—About 35.6 cm.

*Flowering stem (peduncle) length.*—About 40.2 cm.

*Flowering stem diameter.*—About 2.6 mm.

*Flowering stem internode length.*—About 2.3 cm.

*Flowering stem texture.*—Moderately pubescent.

*Flowering stem color.*—Closest to 144A.

*Foliage description.*—Arrangement: Opposite, simple; sessile. Leaves per flowering stem: About 32. Length: About 7.8 cm. Width: About 1.2 cm. Shape: Linear. Apex: Acute. Base: Acute. Margin: Serrate to dentate. Texture, upper and lower surfaces: Moderately pubescent. Venation pattern: Pinnate. Color: Upper surface: 146A; venation, 144C. Lower surface: 146B; venation, 144C.

Flower description:

*Flower type and flowering habit.*—Single bi-labiate arranged on axillary racemes; flowers opposite. Usually about 15 open flowers per raceme. Flowers face outwardly. Flowers self-cleaning. Flowers not fragrant.

*Flower longevity.*—Flowers last about five to seven days on the plant.

*Natural flowering season.*—Flowering is continuous from spring until fall.

*Raceme length.*—About 19.5 cm.

*Flower diameter.*—About 2.3 cm by 2.2 cm.

*Flower tube length.*—About 9 mm.

*Flower buds.*—Diameter: About 6.4 mm. Shape: Ovate. Color: N87C.

*Petals.*—Quantity: Five per flower, fused at base. Shape: Obovate. Apex: Rounded. Margin: Entire. Texture, upper and lower surfaces: Mostly smooth; pubescence around rim of throat and at base of lobes. Color: Upper petals, upper surface: N87A; becoming closer to 86A with development. Upper petals, lower surface: N87A; becoming closer to 86B with development. Lateral petals, upper surface: N87A; becoming closer to 86A with development. Lateral petals, lower surface: N87A; becoming closer to 86B with development. Lower petal, upper surface: N87A; becoming closer to 86A with development. Lower petal, lower surface: N87A; becoming closer to 86B with development. Palate: 155D; becoming closer to N81A with development. Throat: N80A with spots, N81A. Tube: 83A; at calyx, N81A.

*Sepals.*—Quantity/arrangement: Five per flower; fused at base; non-imbricate. Length: About 4 mm. Width: About 2 mm. Calyx length: About 5 mm. Calyx diameter: About 6 mm. Shape: Lance-shaped. Apex: Acuminate. Texture, upper and lower surfaces: Densely pubescent Color, upper surface: 147A. Color, lower surface: 147B.

*Pedicels.*—Length: About 1.2 cm. Diameter: Less than 1 mm. Strength: Strong; flexible. Angle: Acute. Texture: Densely pubescent. Color: 144A overlain with 183A.

*Reproductive organs.*—Androecium: Stamen quantity: Four per flower. Stamen length: About 2 mm. Stamen color: N87B. Anther length: About 1 mm. Anther shape: Fan-shaped. Anther color: N87B. Pollen amount: Moderate. Pollen color: 155D. Gynoecium: Pistil quantity: One per flower. Pistil length: About 5 mm. Style length: About 2 mm. Style color: 155D overlain with N87B. Stigma length: Less than 1 mm. Stigma color: Colorless, clear. Ovary length: About 3 mm. Ovary color: 155D overlain towards base with N87B.

*Seeds/fruits.*—Seed and fruit development has not been observed.

Disease/pest resistance: Plants of the new Angelonia have not been observed to be resistant to pathogens and pests common to Angelonia.

It is claimed:

1. A new and distinct cultivar of Angelonia plant named 'Balangdepi', as illustrated and described.

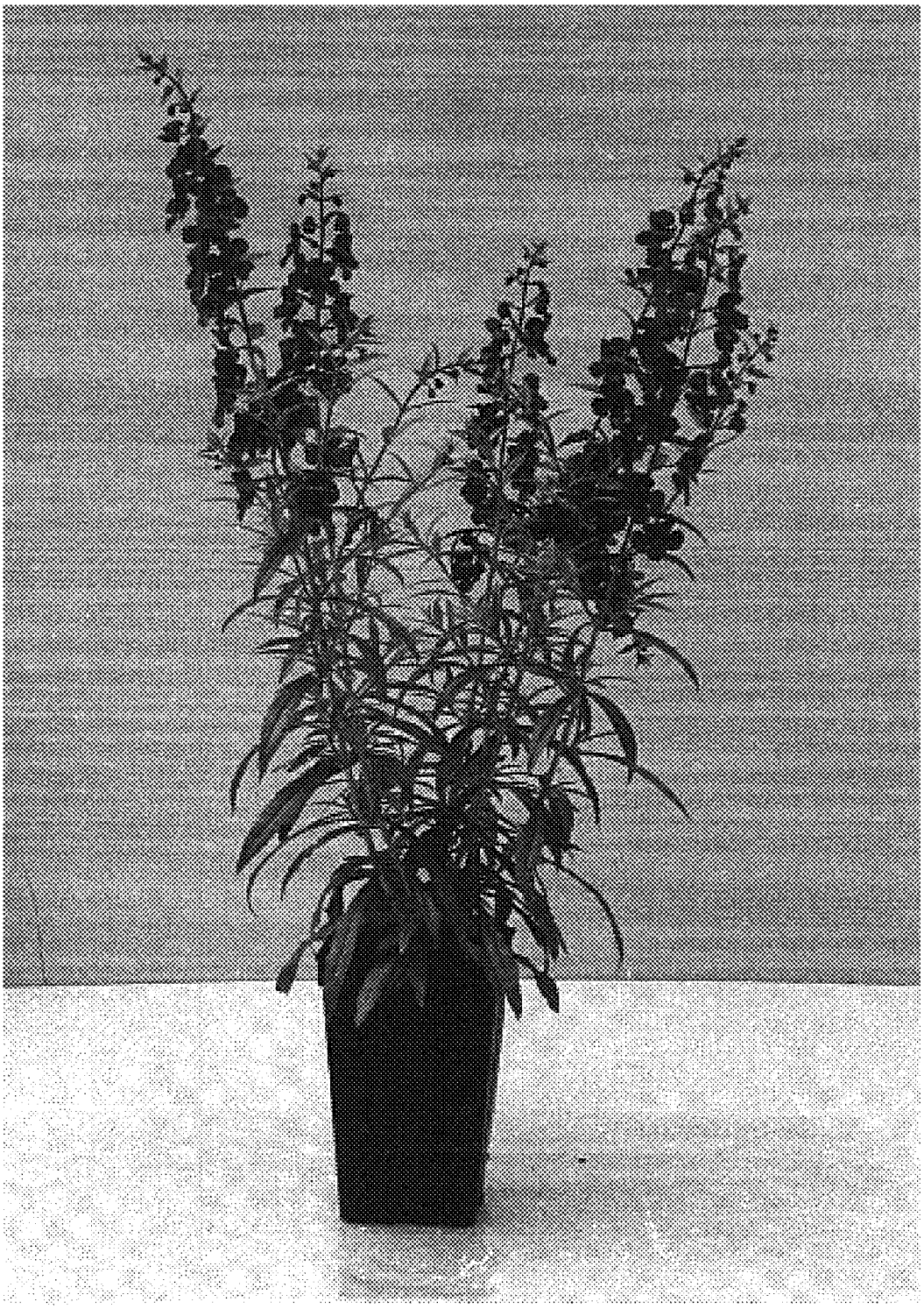

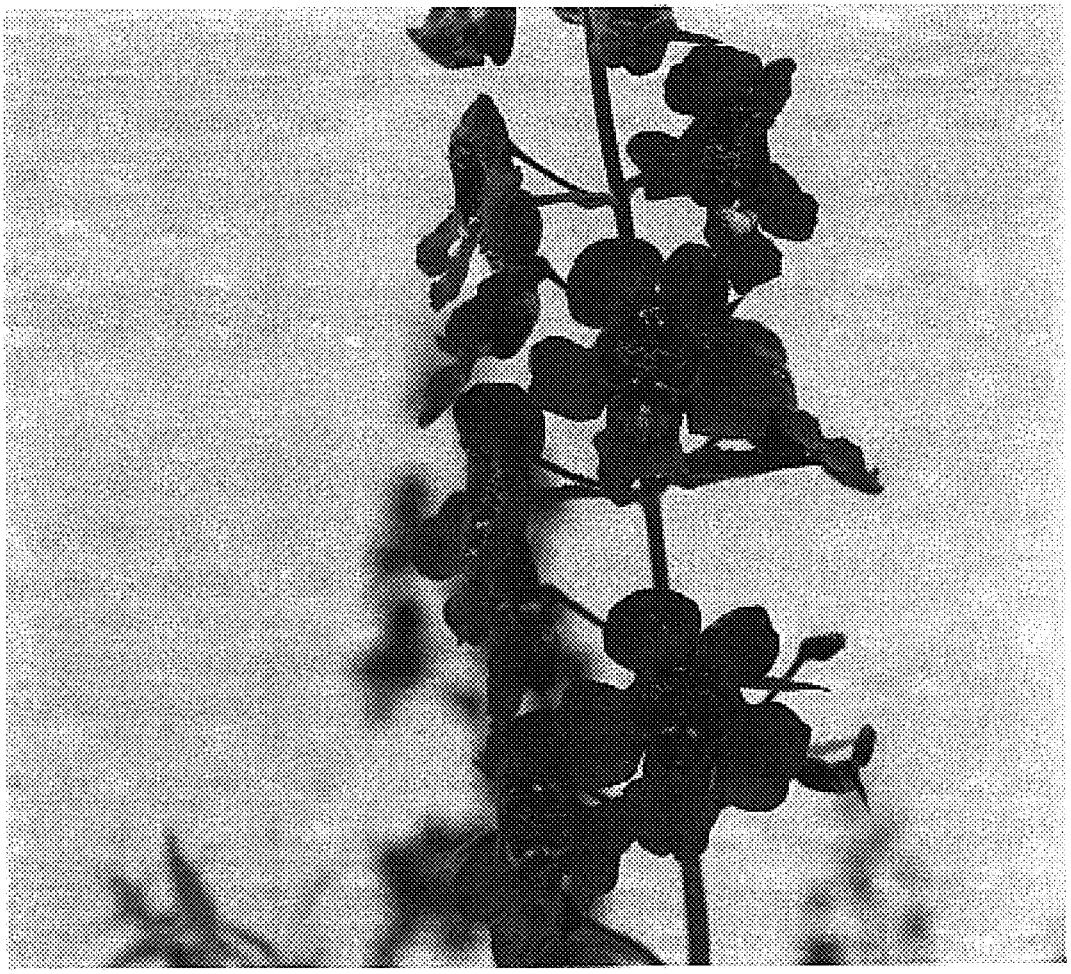

* * * * *